(12) United States Patent
Lavchiev et al.

(10) Patent No.: US 9,618,693 B2
(45) Date of Patent: Apr. 11, 2017

(54) LIQUID SENSING SYSTEMS AND METHODS USING A RING RESONATOR SENSOR

(71) Applicant: Infineon Technologies AG, Neubiberg (DE)

(72) Inventors: Ventsislav Lavchiev, Gallneukirchen (AT); Bernhard Jakoby, Linz (AT); Ursula Hedenig, Villach (AT); Thomas Grille, Villach (AT); Peter Irsigler, Obernberg am Inn (AT); Thomas Neidhart, Klagenfurt (AT); Thomas Krotscheck Ostermann, Koestenberg (AT)

(73) Assignee: Infineon Technologies AG, Neubiberg (DE)

( * ) Notice: Subject to any disclaimer, the term of this patent is extended or adjusted under 35 U.S.C. 154(b) by 0 days.

(21) Appl. No.: 14/303,862

(22) Filed: Jun. 13, 2014

(65) Prior Publication Data

US 2015/0362672 A1 Dec. 17, 2015

(51) Int. Cl.
*G01J 5/02* (2006.01)
*G02B 6/10* (2006.01)
*G01N 21/59* (2006.01)
*G01N 21/77* (2006.01)
*G01N 21/552* (2014.01)

(52) U.S. Cl.
CPC ............. *G02B 6/102* (2013.01); *G01N 21/59* (2013.01); *G01N 21/7746* (2013.01); *G01N 21/552* (2013.01); *G01N 2021/7783* (2013.01)

(58) Field of Classification Search
CPC ............... G01N 21/7746; G01N 21/05; G01N 2021/1704; G01N 21/35; G01N 2021/458; G01N 21/53; G01N 21/59; G01N 2201/08; G02B 6/122; G02B 6/102; G02B 6/29341; G02B 6/29332; G02B 6/29334; G02B 6/10
USPC ....................................................... 250/343
See application file for complete search history.

(56) References Cited

U.S. PATENT DOCUMENTS

| 5,390,021 | A | | 2/1995 | Nagata et al. | |
|---|---|---|---|---|---|
| 6,078,705 | A | * | 6/2000 | Neuschafer | G01N 21/6452 385/12 |
| 6,289,144 | B1 | * | 9/2001 | Neuschafer | G01N 21/6452 385/12 |
| 6,510,263 | B1 | * | 1/2003 | Maisenholder | G01N 21/552 385/37 |
| 6,567,753 | B2 | * | 5/2003 | Potyrailo | G01N 21/31 702/39 |
| 6,819,811 | B1 | * | 11/2004 | Goldstein | B82Y 30/00 385/12 |
| 7,289,221 | B2 | * | 10/2007 | Wang | G01N 21/552 356/477 |

(Continued)

*Primary Examiner* — Mark R Gaworecki
*Assistant Examiner* — Taeho Jo
(74) *Attorney, Agent, or Firm* — Eschweiler & Potashnik, LLC

(57) ABSTRACT

A sensor system having a multi-pass interaction region is disclosed. The system includes an input region, a multi-pass region, and an output region. The input region is configured to receive emitted light. The multi-pass region is coupled to the input region and is configured to absorb portions of the emitted light according to a specimen proximate the multi-pass region. The output region is coupled to the multi-pass region and is configured to provide interacted light from the multi-pass region.

23 Claims, 7 Drawing Sheets

(56) References Cited

U.S. PATENT DOCUMENTS

| | | | |
|---|---|---|---|
| 7,352,466 B2 * | 4/2008 | Cao | B82Y 20/00 356/437 |
| 7,579,609 B2 | 8/2009 | Gorrell et al. | |
| 2002/0094150 A1 * | 7/2002 | Lim | B82Y 20/00 385/15 |
| 2003/0133640 A1 * | 7/2003 | Tiefenthaler | G01N 21/648 385/12 |
| 2003/0210396 A1 * | 11/2003 | Hobbs | G02B 5/204 356/416 |
| 2004/0022474 A1 * | 2/2004 | Lim | B82Y 20/00 385/4 |
| 2004/0240768 A1 * | 12/2004 | Depeursinge | A61B 5/1455 385/12 |
| 2005/0210989 A1 * | 9/2005 | Ja | G01L 11/02 73/705 |
| 2006/0066866 A1 * | 3/2006 | Wang | G01N 21/552 356/481 |
| 2006/0072875 A1 * | 4/2006 | Bhagavatula | G02B 6/12007 385/30 |
| 2006/0227331 A1 * | 10/2006 | Vollmer | G01N 21/23 356/483 |
| 2006/0285114 A1 * | 12/2006 | Cao | B82Y 20/00 356/437 |
| 2007/0140638 A1 * | 6/2007 | Yang | G01N 21/05 385/132 |
| 2007/0230870 A1 * | 10/2007 | Smith | G02B 6/12007 385/32 |
| 2007/0237460 A1 * | 10/2007 | Fan | G01N 21/7746 385/39 |
| 2007/0252995 A1 * | 11/2007 | Shaw | G01N 21/552 356/437 |
| 2008/0008418 A1 * | 1/2008 | Smith | G01N 21/648 385/32 |
| 2008/0074673 A1 * | 3/2008 | Tazartes | G01C 19/64 356/470 |
| 2008/0285606 A1 * | 11/2008 | Kippenberg | G02F 1/39 372/32 |
| 2010/0014544 A1 * | 1/2010 | Heideman | H01S 5/065 372/20 |
| 2010/0124787 A1 * | 5/2010 | Nitkowski | G01N 21/7746 436/164 |
| 2010/0165351 A1 * | 7/2010 | Xu | G01N 21/7703 356/477 |
| 2012/0062902 A1 * | 3/2012 | Digonnet | G01C 19/722 356/483 |
| 2012/0308181 A1 * | 12/2012 | Hafezi | G02B 6/12007 385/31 |
| 2013/0121633 A1 * | 5/2013 | Painter | G02B 26/001 385/14 |
| 2013/0261010 A1 * | 10/2013 | Bailey | G01N 27/72 506/9 |

* cited by examiner

700

LIQUID SENSING SYSTEMS AND METHODS USING A RING RESONATOR SENSOR

BACKGROUND

Sensors are utilized in sensing systems to detect properties, such as light, temperature, motion, and the like. One type of sensor is a fluid (liquid or/and gas) sensor, which is operable to sense fluids. Measurements are performed by the sensor on some certain property of the fluid and these measurements are then used to determine the type of the fluid itself or to determine another property of the fluid.

A common sensor is an absorption sensor used for measuring fluids and a typical configuration is a straight waveguide. The straight waveguide configuration uses a straight ridge (rib) through which light passes. The ridge is in contact with a specimen. An output port of the waveguide provides exiting light and the output signal changes when the light in the waveguide interacts with the fluid atop. These variations can be measured and correlated to fluids.

However, such waveguides are relatively insensitive and require very long lengths in order to sufficiently identify varied liquids. Alternatively to increase the sensitivity, multiple waveguides are generally needed and formed as a mesh. This mesh construction is fragile and, as a result, susceptible to damage. An improved sensor is needed.

DETAILED DESCRIPTION

Figure 1:
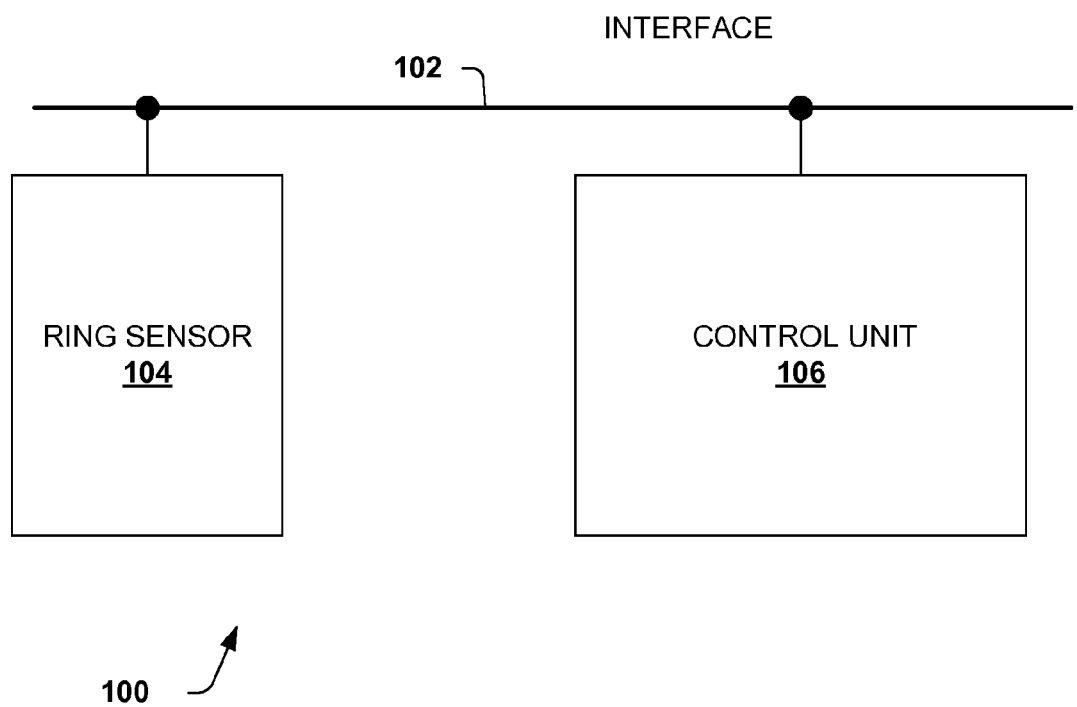
FIG. 1 is a diagram of a sensor system using a ring waveguide.

The present invention will now be described with reference to the attached drawing figures, wherein like reference numerals are used to refer to like elements throughout, and wherein the illustrated structures and devices are not necessarily drawn to scale.

Sensor systems and methods are disclosed utilizing sensors having multi-pass regions being with straight and/or bended shapes. The multi-pass regions allow multiple passes of light through an interaction volume, which means multiple interactions between the light and the sample. The size, shape and composition of the waveguide can be varied or adjusted to measure different types of liquids and gases.

FIG. 1 is a diagram of a sensor system 100 using a ring waveguide. The system 100 is provided in a simplified form in order to aid understanding. The system 100 is provided as an example of a system using a ring sensor for sensing liquids or gasses.

The system 100 includes an interface 102, a ring sensor 104 and a control unit 106. The interface 102 couples the ring sensor 104 to the control unit 106. The interface 102 can be configured to provide power and/or signals for communication.

The control unit 106 is configured to control the ring sensor 104 and to obtain and utilize measurements generated by the ring sensor 104. For example, the control unit 106 can be configured, in one example, to determine a liquid and a composition of the liquid based on a measurement or output signal from the ring sensor 104.

The ring sensor 104 is configured to measure and/or detect specimen(s) proximate the ring sensor 104. The sensor 104 can be configured to measure chemical and/or environmental properties of a specimen proximate the sensor 104. The specimen can be placed or located in contact with the sensor 104.

The sensor 104 includes a bended or ring shaped waveguide. Some examples of suitable shapes are provided below. A light source is coupled to an input of the waveguide and a light detector is coupled to an output of the waveguide. Light passes through the bended or ringed shaped interaction region multiple times. As the light passes, attenuation of the light occurs. This attenuation varies according to a specimen in contact with or proximate to the interaction region. The detector measures the output light. This information or measurement can be provided to the control unit 106 for analysis. The measurement correlates to the specimen and includes, for example, specimen type, liquid, gas, temperature, and the like.

Figure 2:
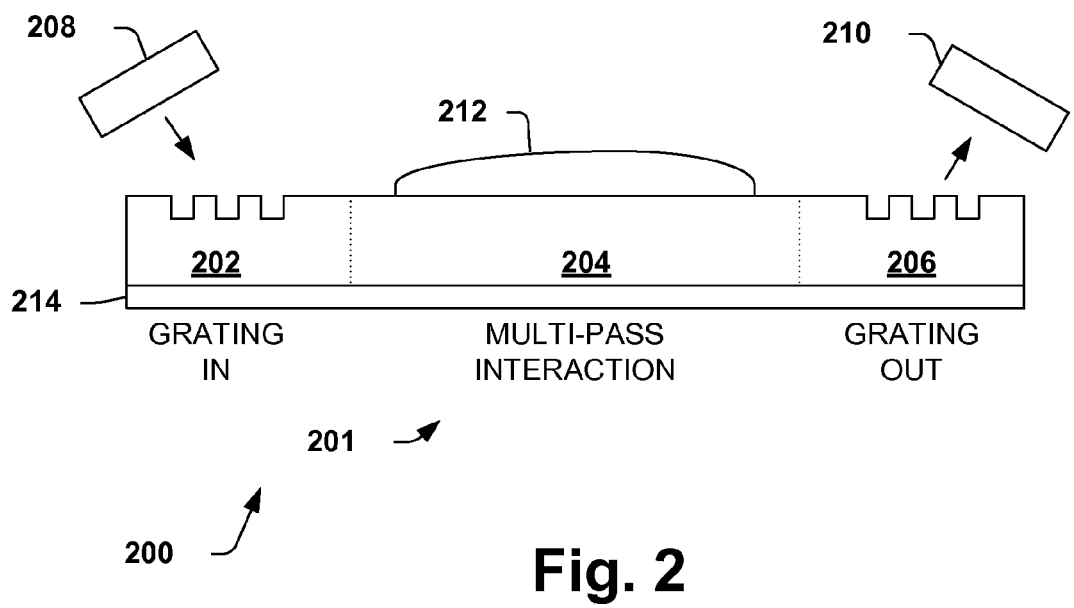
FIG. 2 is a diagram illustrating a side view of a multi-pass, ring waveguide sensor.

FIG. 2 is a diagram illustrating a side view of a multi-pass waveguide sensor 200. The sensor 200 is utilized to detect and/or measure fluid proximate to the sensor 200. The sensor 200 uses a multi-pass region where light passes through multiple times in order to enhance the absorption rate and reduce a size for the sensor.

The sensor 200 includes a waveguide 201, a light source 208, and a light detector 210. The light source 208 emits an electromagnetic field (or light). The light source 208 can be configured to emit a particular wavelength of light, such as infra red. The detector 210 is configured to detect or measure the wavelength of light emitted by the light source 208 after it passes through the waveguide 201. A specimen 212 is located proximate to or in contact with the waveguide 201. The specimen 212 can include a liquid and/or a gas.

The waveguide 201 includes an input region 202, a multi-pass interaction region 204 and an output region 206 and is formed on a membrane 214. The waveguide 201 is comprised of a suitable material, such as silicon, and has a suitable dimension. In one example, the waveguide 201 has a width of 2 micrometers and a height of 600 nanometers. Other characteristics for the waveguide 201 can also be selected or adjusted including, but not limited to, used ports, ring or disc shape for the interaction region 204, materials, and the like. Further, the waveguide 201, in one example, is a rib waveguide as a guiding medium. The rib waveguide confines light passing through in two dimensions. In another example, the waveguide is or is formed in a photonic crystal or segmented waveguide that has periodic changes in its cross section/refractive index. The photonic crystal or segmented waveguide can be formed with 2D or 3D patterning.

Generally, photonic crystal is a periodic structure of two types: air holes in a material slab and material rods in air. For air holes in a material slab, the air holes are arranged in a periodic lattice. For material rods in air, the rods are arranged in a periodic lattice. An example of a photonic crystal is described below. The holes in the slab can be filled with material having different index of refraction in comparison to the material of the slab.

The input region 202 receives the emitted light from the light source 208 and directs the light to the multi-pass interaction region 204. In one example, the light source 208 is positioned off plane with respect to the waveguide 201 and the input region 202 is configured with a grating to allow the light to enter the waveguide 201. In another example, the light source 208 is positioned so that to direct the emitted light through the waveguide 201. The grating has suitable dimensions, such as a grating period, grating height and length of grating region (e.g., 2 mm), in order to allow sufficient light to enter the waveguide 201. In yet another example, the light source 208 resides on a same chip as the waveguide 201 and is in-line with the waveguide 201.

The membrane 214 is comprised of a suitable material for supporting the waveguide 201 and, typically, a number of other waveguides/sensors. Additionally, the suitable material is selected to provide membrane characteristics including, for example, index of refraction, flexibility, and the like. The membrane 214 can be somewhat rigid or flexible, depending on the materials used. In one example, the membrane 214 includes a honeycomb structure on its back side with respect to the waveguide, which facilitates strength while permitting flexibility. In one example, the suitable material is Silicon Nitride. In another example, the suitable material has a low refractive index.

The multi-pass interaction region 204, also referred to as a resonator region, includes a ring or bended shape configured to cause the guided light to pass or propagate through multiple times. The ring shape and size is configured for a selected wavelength and absorption rate. As the guided light passes through the absorption region, the guided light is attenuated according to the specimen 212. Thus, varied specimen types and characteristics, such as age and temperature, yield different absorption rates through the region. As a result, the guided light exits the multi-pas interaction region 204 attenuated. The interacted light is attenuated when compared with the emitted light or with the light without the specimen 212.

The interacted light exits the waveguide 201 at the output region 206. The interacted light is measured by the detector 210. In one example, the output region 206 has grating to allow the interacted light to exit the waveguide 201. In another example, the output region 206 has an exit or opening positioned in line with the detector 210. For example, the detector can be formed on a chip with and in-line with the waveguide 201.

The detector 210 measures the exiting light from the output region 206 of the waveguide 201. The exiting light is attenuated compared with the emitted light or with the light without the specimen 212. The detector 210 or another component, such as a controller, uses the measured light to determine a composition and other characteristics of the specimen 212. The detector 210 can be configured to be in line with the waveguide 201. Alternately, the detector 210 can be configured to be off plane/line with the waveguide.

The detector 210 can be configured to measure a selected range or wavelengths of light, such as infrared. In one example, the waveguide 200 is configured to sense wavelengths of around 5-6 micro-meters.

It is noted that the waveguide 201 can be configured to provide a wavelength or range of wavelengths, referred to as an output wavelength, which can be a subset of the wavelengths of the emitted light. In essence, the waveguide 201 can be configured to filter out or attenuate other wavelengths by selection of ports used, radius/period size (in photonic crystal case), region 204 shape and size, materials used, and the like.

Figure 3A:
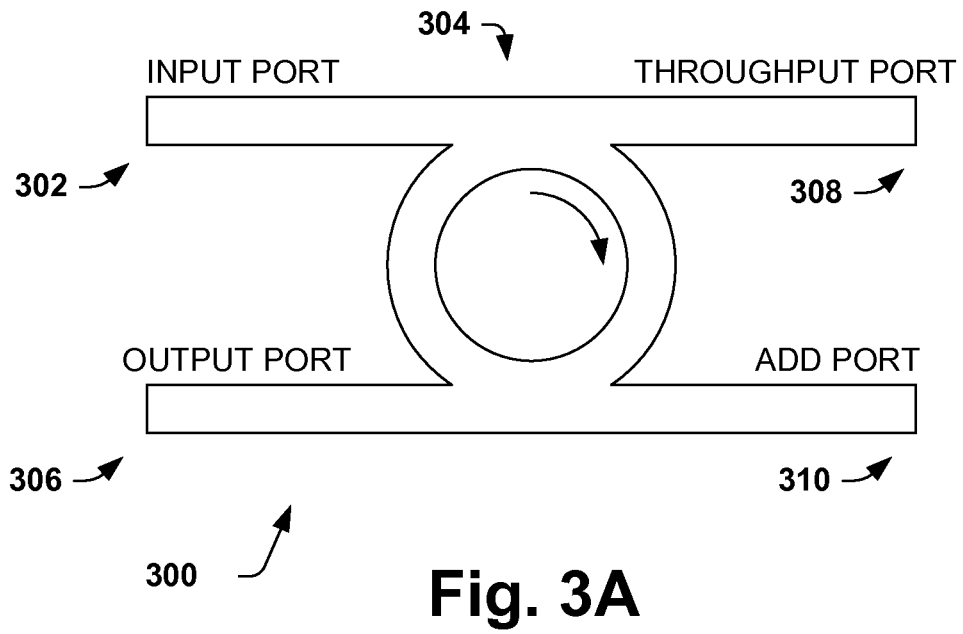
FIG. 3A is a diagram illustrating a ring shaped multi-pass waveguide 300 having four ports.

FIG. 3A is a diagram illustrating a ring shaped multi-pass waveguide 300 having four ports. The waveguide 300 can be incorporated into the sensor 200 described above in order to measure or detect a specimen. The waveguide 300 includes a multi-pass or resonator region that enhances the absorption rate of the waveguide 300 without consuming substantial area.

The waveguide 300 includes an input port 302, a multi-pass interaction region 304, an output port 306, a throughput port 308, and an add/drop port 310. In this example, the throughput port 308 and the add port 310 are shown, but not used. It is appreciated that variations of the waveguide 300 can utilize the throughput port 308 and/or the add port 310 for added functionality.

The input port 302 receives the emitted light from a light source and directs the light to the multi-pass interaction region 304. In one example, the input port 302 is configured with a grating to allow the light to enter. In another example, the light source is positioned in line with the input port 302 to feed the emitted light into the input port 302.

The multi-pass interaction region 304, also referred to as a resonator region, includes a ring or bended shape configured to cause the guided light to pass through (e.g., circulate) multiple times. An arrow in FIG. 3 illustrates the general rotation of light through the region 304. The ring shape and size is configured for a selected wavelength and absorption rate. As the light passes or propagates through the absorption, interaction region 304, the light is attenuated according to a specimen proximate the interaction region 304. The amount and/or rate of attenuation depends on the specimen and characteristics of the specimen. For example, varied specimen types and characteristics, such as composition, temperature or age of the fluid, yield different absorption rates through the region. As a result, interacted light exits the multi-pas interaction region 304. The interacted light is attenuated when compared with the emitted light or with the light without the specimen 212.

The interacted light exits the region 304 and exits the waveguide 300 via the output port 306. The interacted light is measured by a detector, such as the one shown above. In one example, the output port 306 has a grating to allow the interacted light to exit the waveguide 300. In another example, the output port 306 has an exit or opening positioned in line with the detector.

It is noted that the configuration of the waveguide 300 prevents light from passing directly through the waveguide 300, as can happen with other straight line waveguides.

Figure 3B:
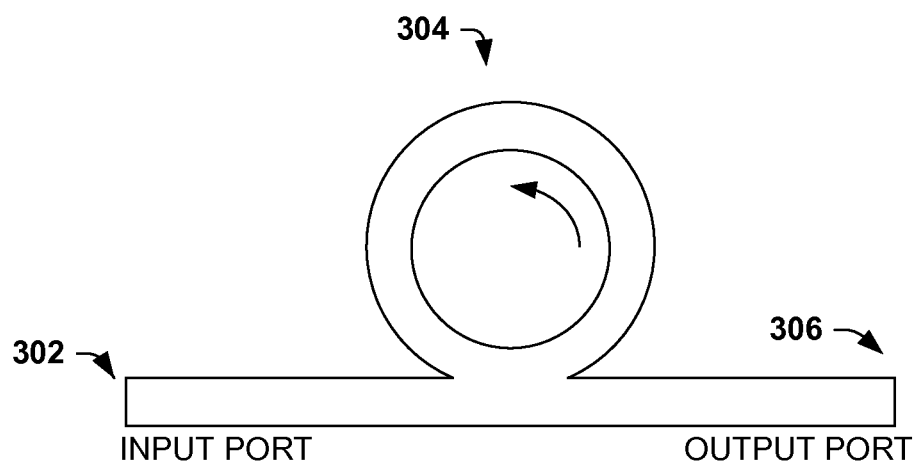
FIG. 3B is a diagram illustrating a ring shaped multi-pass waveguide having two ports.

FIG. 3B is a diagram illustrating a ring shaped multi-pass waveguide 300 having two ports. The waveguide 300 can be incorporated into the sensor 200 described above in order to measure or detect a specimen. The waveguide 300 includes a multi-pass or resonator region that enhances the absorption rate of the waveguide 300 without consuming substantial area.

The waveguide 300 includes an input port 302, a multi-pass interaction region 304, and an output port 306. The input port 302 receives the emitted light from a light source, propagates it along the straight waveguide and couples the light into the ring 304. After being trapped in the ring 304

(where interaction with the specimen takes place), the partially attenuated light is coupled out to the straight waveguide toward the output port. In one example, the input port 302 is configured with grating to allow the light to enter. In another example, the light source is positioned in line with the input port 302 to direct the emitted light into the input port 302.

The multi-pass interaction region 304, also referred to as a resonator region, includes a ring or bended shape configured to cause the emitted light to pass through multiple times. An arrow in FIG. 3B illustrates the general rotation/propagation of light through the region 304. The ring shape and size is configured for a selected wavelength and absorption rate. As the emitted light passes through the absorption, interaction region 304, the emitted light is attenuated according to a specimen proximate the interaction region 304. The amount and/or rate of attenuation varies according to the specimen and characteristics of the specimen. For example, varied specimen types and characteristics, such as age of sample and temperature, yield different absorption rates through the region. As a result, interacted light exits the multi-pas interaction region 304. The interacted light is attenuated when compared with the emitted light or with the light without the specimen 212.

The interacted light exits the region 304 and exits the waveguide 300 via the output port 306. The interacted light is measured by a detector, such as the one shown above. In one example, the output port 306 has grating to allow the interacted light to exit the waveguide 300. In another example, the output port 306 has an exit or opening positioned in line with the detector.

It is noted that the configuration of the waveguide 300 of FIG. 3B permits light to pass directly through the waveguide 300. Additionally, the light travels throughout the multi-pass region 304 counter clockwise as viewed from the top.

Figure 4A:
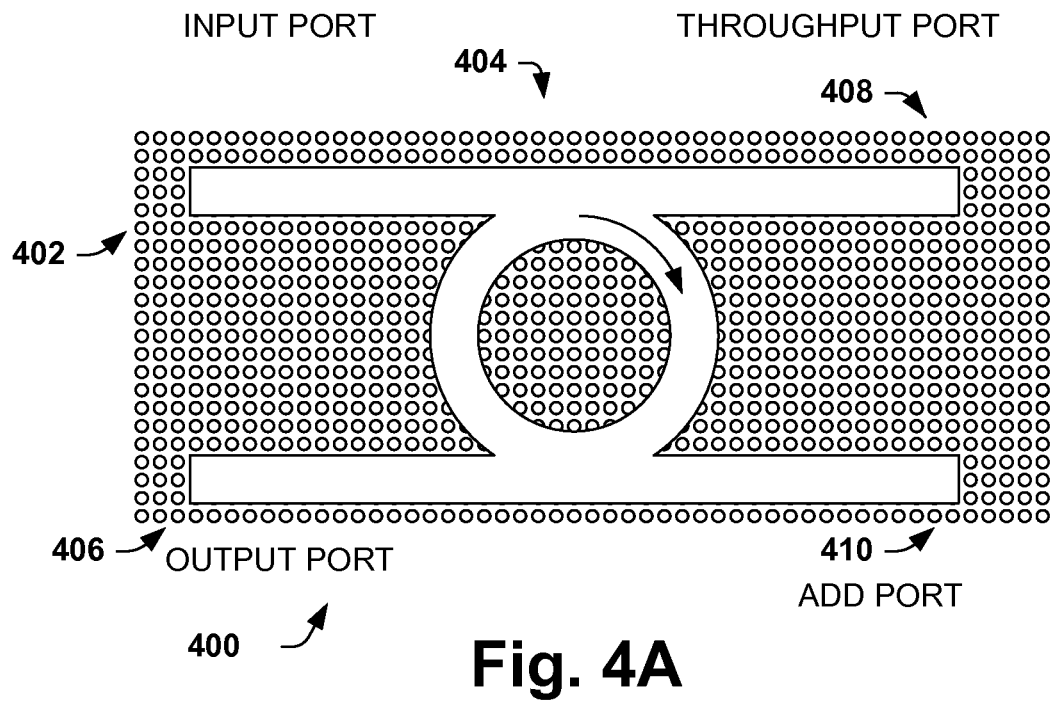
FIG. 4A is a diagram illustrating a ring shaped multi-pass waveguide realized by a photonic crystal and having four ports.

FIG. 4A is a diagram illustrating a ring shaped multi-pass waveguide 400 realized as a photonic crystal (PhC) and having four ports. The waveguide 400 can be incorporated into the sensor 200 described above in order to measure or detect a specimen. The waveguide 400 includes a PhC multi-pass or resonator region that enhances the absorption rate of the waveguide 400 without consuming substantial area.

The waveguide 400 is formed using photonic crystal. An example pattern is shown to illustrate the photonic crystal, however it is appreciated that the pattern is for illustrative purposes and that other patterns can be utilized. The pattern is two or three dimensional and is configured for characteristics including, but not limited to, wavelength, absorption, transmittance and the like. The waveguide 400 is shown with a cubic lattice, however other configurations including, but not limited to, a hexagonal lattice, hexagonal ring, and the like can be utilized.

The waveguide 400 utilizes or is formed from a suitable material. In one example, the photonic crystal and/or the waveguide 400 is formed on a silicon wafer. Additionally, an epoxy resin and/or Imide can be used as a photonic layer within the waveguide 400. Another material that can be used for the waveguide 400 is PMMI (Polymethacrylmethylimide)—an amorphous, crystal clear plastic having a transmittance of 90% at a thickness of 3 mm. The refractive index for the PMMI increases with higher concentrations of Imide.

The waveguide 400 includes an input port 402, a multi-pass PhC interaction region 404, an output port 406, a throughput port 408, and an add/drop port 410. The throughput port 408 and the add port 410 are shown, but not used. It is appreciated that variations of the waveguide 400 can utilize the throughput port 408 and/or the add port 410 for added functionality. The functionality of the waveguide 400 is similar to that of the waveguide 300 described in FIG. 3A.

The input port 402 receives the emitted light from a light source and directs the light to the multi-pass interaction region 404. In one example, the input port 402 is configured with a grating to allow the light to enter. In another example, the light source is positioned in line with the input port 402 to feed the emitted light into the input port 402.

The multi-pass interaction region 404, also referred to as a PhC resonator region, includes a ring or bended shape configured to cause the guided light to pass through (e.g., circulate) multiple times. An arrow in FIG. 4A illustrates the general rotation of light through the region 404. The ring shape and size is configured for a selected wavelength and absorption rate. As the light passes or propagates through the absorption, interaction region 404, the light is attenuated according to a specimen proximate the interaction region 404. The amount and/or rate of attenuation depends on the specimen and characteristics of the specimen. For example, varied specimen types and characteristics, such as composition, temperature or age of the fluid, yield different absorption rates through the region. As a result, interacted light exits the multi-pas interaction region 404. The interacted light is attenuated when compared with the emitted light.

The interacted light exits the region 404 and exits the waveguide 400 via the output port 406. The interacted light is measured by a detector, such as the one shown above. In one example, the output port 406 has a grating to allow the interacted light to exit the waveguide 400. In another example, the output port 406 has an exit or opening positioned in line with the detector.

Figure 4B:
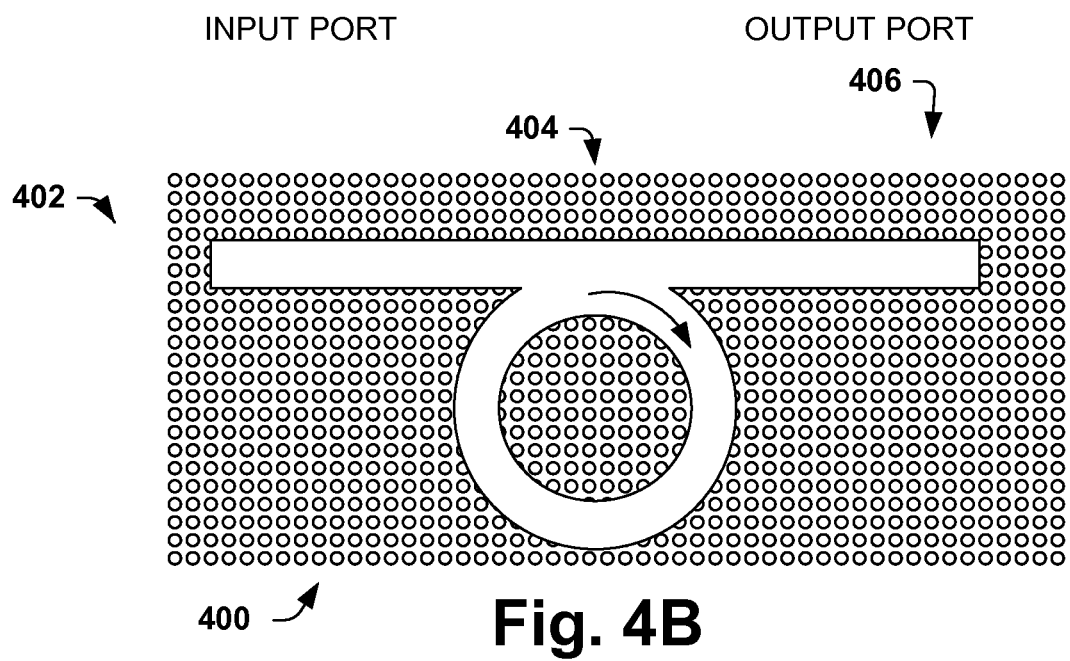
FIG. 4B is a diagram illustrating a ring shaped multi-pass waveguide realized by a photonic crystal and having two ports.

FIG. 4B is a diagram illustrating a ring shaped multi-pass waveguide 400 using photonic crystal and having four ports. The waveguide 400 can be incorporated into the sensor 200 described above in order to measure or detect a specimen. The waveguide 400 includes a multi-pass or resonator region that enhances the absorption rate of the waveguide 400 without consuming substantial area.

The waveguide 400 is formed using photonic crystal. An example pattern is shown to illustrate the photonic crystal, however it is appreciated that the pattern is for illustrative purposes and that other patterns can be utilized. The pattern is two or three dimensional and is configured for characteristics including, but not limited to, wavelength, absorption, and the like. The waveguide 400 is shown with a cubic lattice, however other configurations including, but not limited to, a hexagonal lattice, hexagonal ring, and the like can be utilized.

The waveguide 400 utilizes or is formed from a suitable material. In one example, the photonic crystal and/or the waveguide 400 is formed on a silicon wafer. Additionally, an epoxy resin and/or Imide can be used as a photonic layer within the waveguide 400. Another material that can be used for the waveguide 400 is PMMI (Polymethacrylmethylimide)—an amorphous, crystal clear plastic having a transmittance of 90% at a thickness of 3 mm. The refractive index for the PMMI increases with higher concentrations of Imide.

The waveguide 400 includes an input port 402, a PhC multi-pass interaction region 404, and an output port 406. The input port 402 receives the emitted light from a light source, propagates it along the straight waveguide and couples the light into the ring 404. After being trapped in the ring 404 (where interaction with the specimen takes place), the partially attenuated light is coupled out to the straight waveguide toward the output port. In one example, the input port 402 is configured with grating to allow the light to enter.

In another example, the light source is positioned in line with the input port 402 to direct the emitted light into the input port 402.

The multi-pass interaction region 404, also referred to as a resonator region, includes a ring or bended shape configured to cause the emitted light to pass through multiple times. An arrow in FIG. 4B illustrates the general rotation of light through the region 404. The ring shape and size is configured for a selected wavelength and absorption rate. As the emitted light passes through the absorption, interaction region 404, the emitted light is attenuated according to a specimen proximate the interaction region 404. The amount and/or rate of attenuation varies according to the specimen and characteristics of the specimen. For example, varied specimen types and characteristics, such as age of sample and temperature, yield different absorption rates through the region. As a result, interacted light exits the multi-pas interaction region 404. The interacted light is attenuated when compared with the emitted light or with the light without the specimen 212.

The interacted light exits the region 404 and exits the waveguide 400 via the output port 406. The interacted light is measured by a detector, such as the one shown above. In one example, the output port 406 has grating to allow the interacted light to exit the waveguide 400. In another example, the output port 406 has an exit or opening positioned in line with the detector.

It is noted that the configuration of the waveguide 400 light may pass directly through the waveguide 400. Additionally, the light travels throughout the multi-pass region 404 clockwise as viewed from the top.

Figure 5:
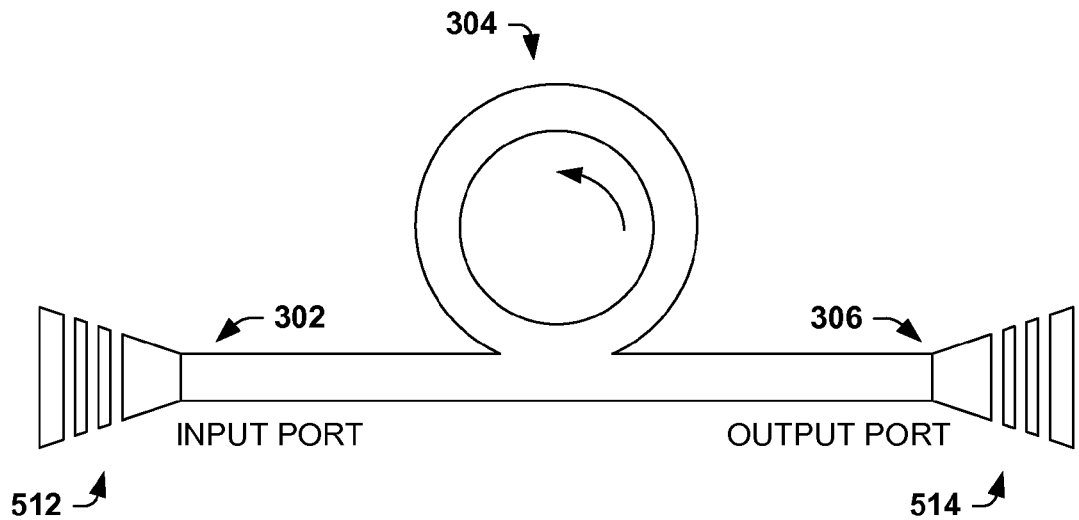
FIG. 5 is a diagram of a waveguide having tapered grating regions.

FIG. 5 is a diagram of a waveguide 300 having tapered grating regions. The waveguide 300 is depicted with the tapered grating regions. It is appreciated that other waveguides having multi-pass regions can utilize the tapered grating regions, including, for example the waveguide 300 of FIG. 3B.

The waveguide 300 includes an input port 302, a multi-pass region 304, and an output port 306. The input port 302 is coupled to or includes an input tapered grating region 512. The output port 306 is coupled to or includes an output tapered grating region 514.

The grating region 512 has a tapered shape that narrows towards the waveguide 300. The tapered shape permits a light source having a wider dispersion of the beam or simply a bigger beam diameter with respect to the width of the waveguide 300. For example, the tapered shape allows for an increase of the amount of light from the source coupled into the waveguide 300 via the input port. As a result, a less restrictive light source can be utilized. The grating includes spaced or separated openings within the region and is configured to allow light to enter the waveguide 300. Sections are present between the openings within the grating region 512. As shown, the grating also includes a tapered shape. The grating is configured to have a diffraction order, which depends on the dimensions of the openings.

The output grating region 514 also has a tapered shape and it expands or increases away from the waveguide 300. The tapered shape disperses light exiting the waveguide 300 and permits a larger sized detector to be utilized.

Figure 6:
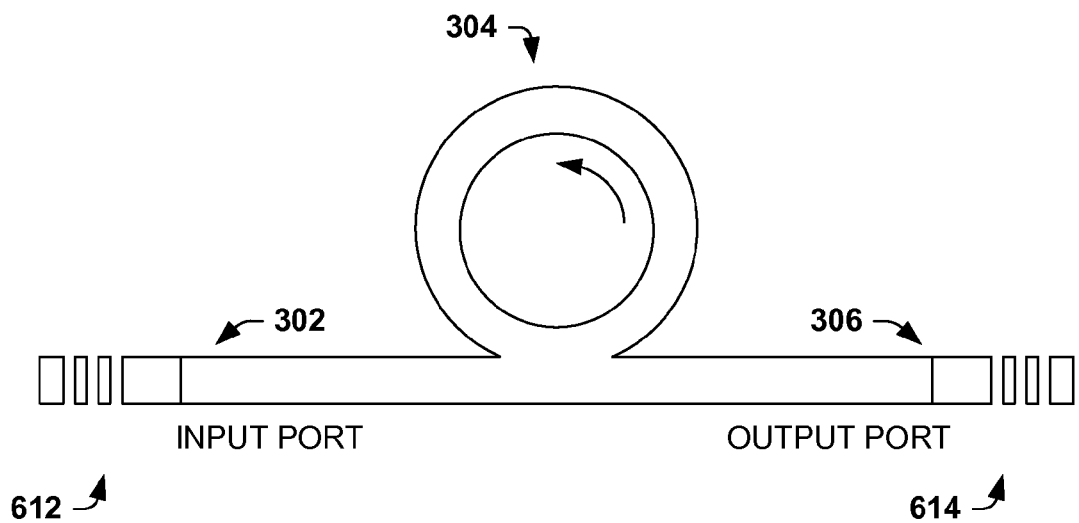
FIG. 6 is a diagram of a waveguide having linear or non-tapered grating regions.

FIG. 6 is a diagram of a waveguide 300 having linear or non-tapered grating regions. The waveguide 300 is depicted here with the linear grating regions. It is appreciated that other waveguides having multi-pass regions can utilize the linear grating regions, including, for example the waveguide 300 of FIG. 3B.

The waveguide 300 includes an input port 302, a multi-pass region 304, and an output port 306. The input port 302 is coupled to or includes an input grating region 612. The output port 306 is coupled to or includes an output grating region 614.

The grating region 612 has a non-tapered, linear shape that generally matches the waveguide 300. The shape generally requires a matching light source with a narrower dispersion (or a small beam diameter) than the light source used for FIG. 5. The grating is configured to allow light to enter the waveguide 300.

The output grating region 614 also has a linear shape in line with the waveguide 300. The linear shape maintains a narrow width of light exiting the waveguide 300 and permits a smaller sized detector to be utilized.

It is appreciated that variations of the grating regions are contemplated. For example, a tapered input grating region 512 of FIG. 5 can be used with a linear output grating region 614 using the waveguides 400 or 300. As another example, a linear input grating region 612 can be used with a tapered output grating region 514 using the waveguides 400 or 300.

Figure 7:
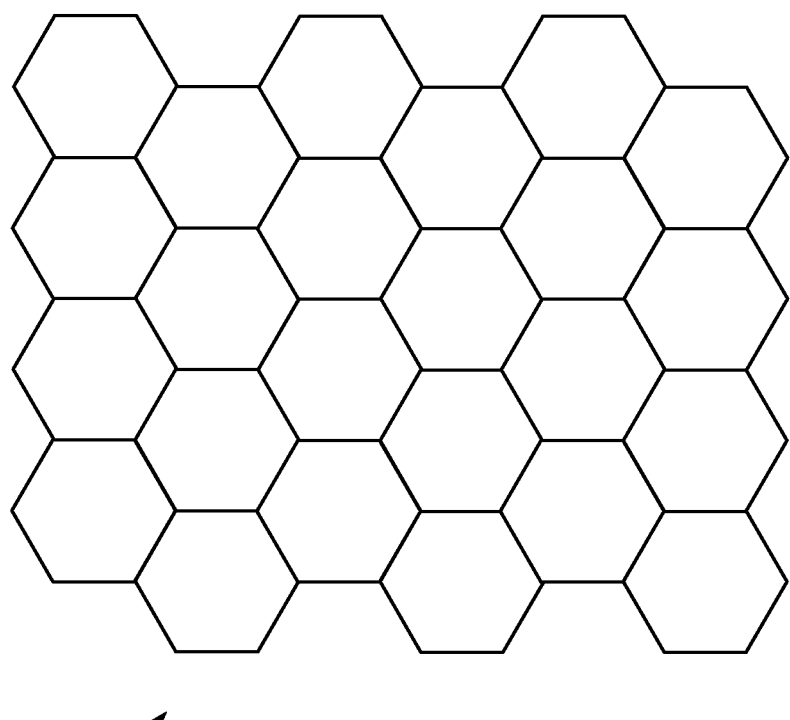
FIG. 7 is a diagram illustrating the substrate of the structure realized as a membrane having hexagon shaped components.

FIG. 7 is a diagram illustrating a membrane 700 having hexagon shaped components. The membrane 700 is used to support or attach thereto one or more waveguides, typically with multi-pass interaction regions. The membrane 700 can be utilized for the membrane 214, described above.

The membrane 700 includes a plurality of hexagon shaped components to form a honeycomb pattern. The individual components can be relatively rigid; however, connection lines between components are bendable and improve flexibility.

The membrane 700 is comprised of a suitable material and has a selected refractive index. The membrane 700 can be configured to support other components including, but not limited to, sensors, light sources, light detectors, interconnects, and the like.

Figure 8:
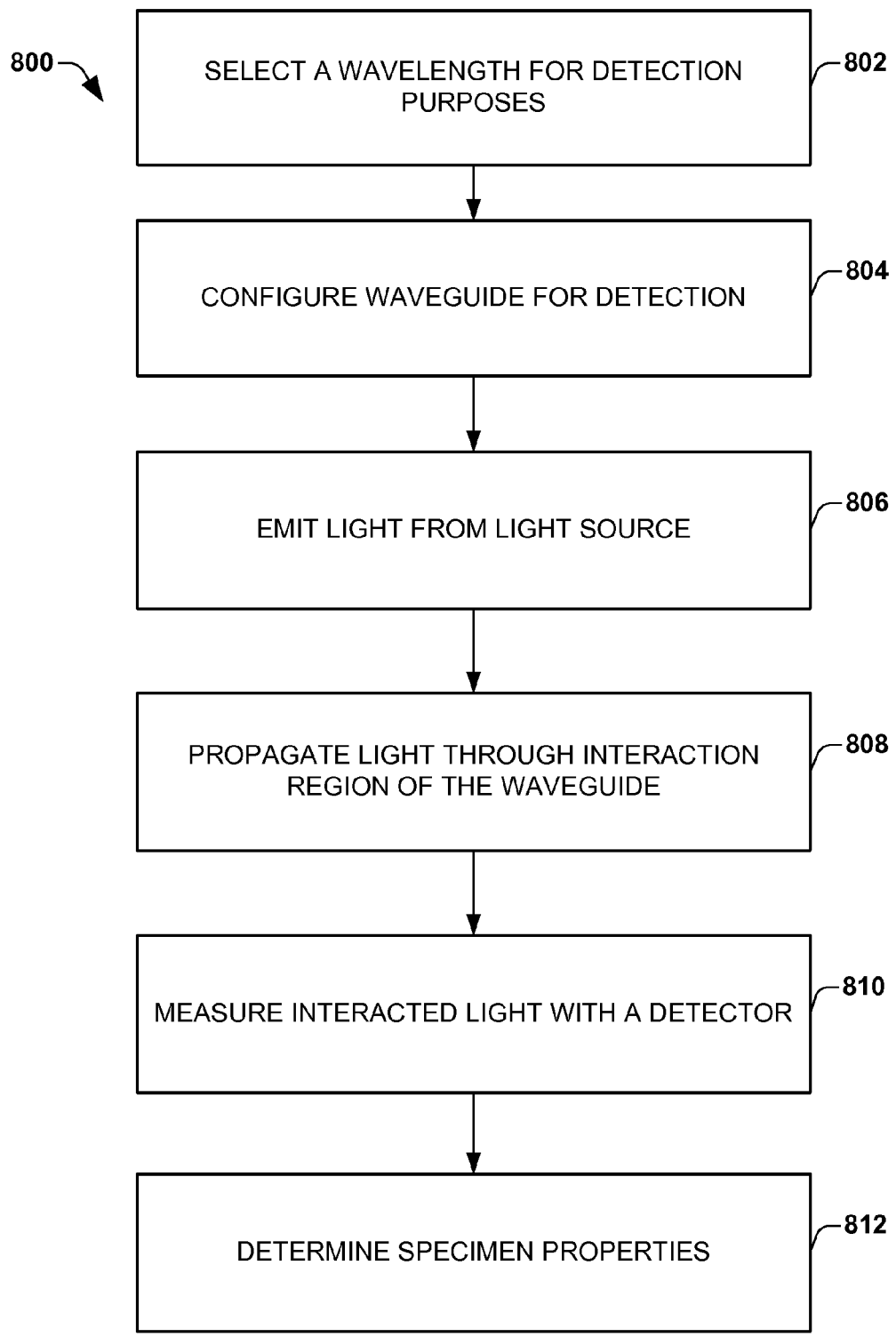
FIG. 8 is a flow diagram illustrating a method of operating a sensor having a multi-pass interaction region.

FIG. 8 is a flow diagram illustrating a method 800 of operating a sensor having a multi-pass interaction region. The method 800 uses multiple passes through an interaction region to reduce space utilized and improve an absorption rate.

The method 800 begins at block 802, where a wavelength or range of wavelengths is selected. The wavelength can be selected according to a specimen and/or types of specimens to be detected. Additionally, the wavelength can be selected to detect particular chemical properties and environmental properties. In one example, the wavelength is selected to only include infra-red light.

A waveguide having a multi-pass interaction region is configured at block 804 according to the selected wavelength. The waveguide is configured to have selected characteristics, such as a selected height width and length. Other selected characteristics can include material, multi-pass region shape, and the like. In one example, the multi-pass interaction region is configured to have a radius selected according to the selected wavelength and/or the chemical and environmental properties to be detected.

A light source emits light having the selected wavelength at block 806. The light source, in one example, is controlled to provide only the selected wavelength. In another example, the light source is designed to emit the selected wavelength. The light source is also configured to emit an amount of light, which is known and can be later used to determine attenuation through the waveguide. Yet in another example, the light source can emit a broad band light and the selection of the wavelength(s) is done via a filter, such as a photonic crystal.

The emitted light passes through the waveguide and the multi-pass interaction region at block 808. As the light makes multiple passes, portions of the light are absorbed by a specimen proximate to the waveguide and the interaction region. The absorption rate depends at least partially on the specimen.

The interacted light exits the waveguide and is measured by a detector at block 810. Once the light makes multiple passes through the waveguide and has interacted with the specimen, the interacted light exits the waveguide through an output region. The light detector captures and measures the light that has interacted and exited the waveguide.

Specimen properties are determined according to the emitted light and the measured light at block 812. The properties include chemical and/or environmental properties. Additionally, the specimen type can be determined at block 812. The light detector and/or a separate controller can be configured to make the determination.

While the method is illustrated and described below as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the disclosure herein. Also, one or more of the acts depicted herein may be carried out in one or more separate acts and/or phases.

It is appreciated that the claimed subject matter may be implemented as a method, apparatus, or article of manufacture using standard programming and/or engineering techniques to produce software, firmware, hardware, or any combination thereof to control a computer to implement the disclosed subject matter (e.g., the systems shown in FIGS. 1, 2, etc., are non-limiting examples of system that may be used to implement the above methods). The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

A sensor system having a multi-pass interaction region is disclosed. The system includes an input region, a multi-pass region, and an output region. The input region is configured to receive emitted light. The multi-pass region is coupled to the input region and is configured to allow absorption of portions of the emitted light according to a specimen proximate the multi-pass region. The output region is coupled to the multi-pass region and is configured to provide interacted light from the multi-pass region.

A sensor system having a multi-pass interaction region is disclosed. The system includes a sensor and a control unit. The sensor includes a light source, a waveguide, and a detector. The light source is configured to emit light at a selected wavelength(s). The waveguide is configured to receive the emitted light, to provide interaction with the specimen and to provide interacted light. The detector is configured to measure the interacted light from the waveguide. The control unit is coupled to the sensor and is configured to determine properties of the specimen according to the measured light and the emitted light.

A method of operating a sensor having a multi-pass interaction region is disclosed. A wavelength for detection is selected. In one example, the wavelength is infra-red. A waveguide with a multi-pass interaction region is configured according to the selected wavelength. Light having the selected wavelength is received at the waveguide. The received light interacts within the multi-pass interaction region. Light exiting the waveguide is measured. The measured light and the received light can be used to determine or detect a specimen.

In particular regard to the various functions performed by the above described components or structures (assemblies, devices, circuits, systems, etc.), the terms (including a reference to a "means") used to describe such components are intended to correspond, unless otherwise indicated, to any component or structure which performs the specified function of the described component (e.g., that is functionally equivalent), even though not structurally equivalent to the disclosed structure which performs the function in the herein illustrated exemplary implementations of the invention. In addition, while a particular feature of the invention may have been disclosed with respect to only one of several implementations, such feature may be combined with one or more other features of the other implementations as may be desired and advantageous for any given or particular application. Furthermore, to the extent that the terms "including", "includes", "having", "has", "with", or variants thereof are used in either the detailed description and the claims, such terms are intended to be inclusive in a manner similar to the term "comprising".

What is claimed is:

1. A sensor system having a multi-pass interaction region, the system comprising:
   an input region configured to receive emitted light;
   a multi-pass region coupled to the input region, wherein the multi-pass region is configured to cause the emitted light to pass through the multi-pass region multiple times and to absorb portions of the emitted light according to a specimen proximate the multi-pass region, and wherein the multi-pass region is comprised of a periodic structure of two types and has an absorption rate based on specimen characteristics and the periodic structure;
   an output region coupled to the multi-pass region, the output region configured to provide interacted light from the multi-pass region; and
   a flexible membrane configured to support the input region, the multi-pass region and the output region, wherein the flexible membrane includes a honeycomb structure on its back side with respect to the input region, the multi-pass region and the output region.

2. The system of claim 1, wherein the input region has a tapered shape.

3. The system of claim 1, wherein the input region has a linear shape.

4. The system of claim 1, wherein the input region has grating configured to receive the emitted light off plane.

5. The system of claim 1, further comprising a light source configured to provide the emitted light at selected wavelengths.

6. The system of claim 1, wherein the emitted light has an infra-red wavelength.

7. The system of claim 1, wherein the multi-pass region has a bend configured to permit multiple passes of at least a portion of the emitted light.

8. The system of claim 1, wherein the multi-pass region is circular and has a radius according to a selected wavelength of the emitted light.

9. The system of claim 1, further comprising a throughput port coupled to the multi-pass region.

10. The system of claim 1, wherein the output region is in-line with the input region.

11. The system of claim 1, further comprising a detector configured to measure the interacted light from the output region.

12. The system of claim 11, further comprising a control unit configured to obtain a measurement of the interacted light from the detector and to determine chemical properties of a specimen proximate the multi-pass region.

13. The system of claim 1, wherein the multi-pass region is comprised of polymethacrylmethylimide (PMMI) and is amorphous and has a transmittance of about 90% at a thickness of 3 mili-meters.

14. The system of claim 1, wherein the absorption rate is further based on temperature and age of the specimen.

15. The system of claim 1, wherein the flexible membrane is comprised of silicon nitride.

16. A sensor system having a multi-pass interaction region, the system comprising:
a sensor having:
a light source configured to emit light at a selected wavelength;
a waveguide formed of photonic crystal and supported by a flexible membrane and configured to receive the emitted light and absorb a portion of the light according to a specimen, and to provide interacted light, wherein the flexible membrane includes a honeycomb structure on its back side with respect to the waveguide, wherein the photonic crystal is a periodic structure of two types of materials arranged in a periodic lattice and has an absorption rate based on specimen characteristics and the periodic structure; and
a detector configured to measure the interacted light from the waveguide; and
a control unit coupled to the sensor and configured to determine properties of the specimen according to the measured light and the emitted light.

17. The system of claim 16, wherein the waveguide has a bended portion configured to cause at least a portion of the emitted light to travel through in multiple passes.

18. The system of claim 16, wherein the waveguide includes a multi-pass interaction region having a circular shape, wherein the circular shape is configured for the selected wavelength.

19. The system of claim 16, further comprising an interface coupled to the sensor and the control unit.

20. A method of operating a sensor having a multi-pass interaction region, the method comprising:
selecting a wavelength for detection;
configuring a waveguide with a multi-pass interaction region according to the selected wavelength, wherein the multi-pass interaction region is a periodic structure of two types of materials arranged in a periodic lattice and has an absorption rate based on specimen characteristics and the periodic structure;
supporting the waveguide with a flexible membrane, wherein the flexible membrane includes a honeycomb structure on its back side with respect to the waveguide;
receiving light having the selected wavelength at the waveguide;
interacting the received light within the multi-pass interaction region; and
measuring the interacted light from the waveguide.

21. The method of claim 20, wherein selecting the wavelength includes selecting the wavelength to detect chemical and environmental properties.

22. The method of claim 20, wherein interacting the received light includes interacting the received light with a specimen proximate to the multi-pass interaction region, wherein the specimen is a liquid.

23. The method of claim 20, further comprising comparing the measured light with the received light to detect a specimen.

* * * * *